United States Patent [19]

Szántay et al.

[11] Patent Number: 4,757,077
[45] Date of Patent: Jul. 12, 1988

[54] BIS-INDOLE DERIVATIVES AND PHARMACEUTICAL COMPOSITIONS CONTAINING THEM

[75] Inventors: Csaba Szántay; Lajos Szabó; Katalin Honty; Tibor Keve; Tibor Acs; Sándor Eckhardt; János Sugar; Zsuzsa Somfai; Éva Iván; Zsuzsa Kneffel, all of Budapest, Hungary

[73] Assignee: Richter Gedeon Vegyeszeti Gyar R.T., Budapest, Hungary

[21] Appl. No.: 873,540

[22] Filed: Jun. 12, 1986

[30] Foreign Application Priority Data

Jun. 12, 1985 [HU] Hungary .............................. 2303/85

[51] Int. Cl.$^4$ .................. A61K 31/475; C07D 519/04
[52] U.S. Cl. ..................................... 514/283; 540/478
[58] Field of Search .......................... 540/478; 514/283

[56] References Cited

U.S. PATENT DOCUMENTS

| | | | |
|---|---|---|---|
| 3,392,173 | 7/1968 | Hargrove | 540/478 |
| 3,450,771 | 6/1969 | Dombro | 568/38 |
| 4,124,646 | 11/1978 | Kawamura et al. | 568/38 |
| 4,191,688 | 3/1980 | Conrad et al. | 540/478 |
| 4,298,525 | 11/1981 | Jovánovics et al. | 540/478 |
| 4,410,459 | 10/1983 | Dancsi et al. | 540/478 |
| 4,621,098 | 11/1986 | Umminger et al. | 514/562 |

Primary Examiner—Donald G. Daus
Assistant Examiner—Diana G. Rivers
Attorney, Agent, or Firm—Keil & Weinkauf

[57] ABSTRACT

The invention relates to novel bis-indole derivatives of the general formula (I)

wherein
$R_1$ stands for a hydrogen atom or an acetyl group;
$R_2$ stands for a hydrogen atom;
$R_3$ means an ethyl group of $\alpha$-position; or
$R_2$ and $R_3$ together represent an oxygen bridge;
$R_4$ represents an ethyl or hydroxyl group of $\beta$-position; and
$R_5$ stands for a hydrogen atom or a hydroxyl group;
A represents a $C_{1-10}$ straight-chain or $C_{3-10}$ branched-chain alkyl group, hydroxy-alkyl, acetyl-alkyl, benzyl, $C_{3-6}$ alkenyl or alkynyl or $C_{5-7}$ cycloalkyl group or an aromatic group or a heteroaromatic group containing one nitrogen or one oxygen atom, and
X stands for oxygen or sulphur atom, as well as their acid addition salts and pharmaceutical preparations containing these compounds.

Further on, the invention relates to a process for preparing these compounds and preparations.

The compounds of the general formula (I) show a cytostatic activity with less toxicity than that of the known vinblastine-type bis-indole alkaloid drugs which are commercially available.

4 Claims, No Drawings

BIS-INDOLE DERIVATIVES AND PHARMACEUTICAL COMPOSITIONS CONTAINING THEM

The invention relates to novel bis-indole derivatives of the general formula (I)

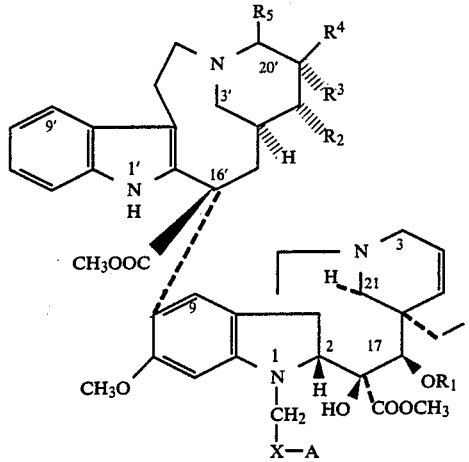

wherein $R_1$ stands for a hydrogen atom or an acetyl group;

$R_2$ stands for a hydrogen atom;

$R_3$ means an ethyl group of α-position; or $R_2$ and $R_3$ together represent an oxygen bridge;

$R_4$ represents an ethyl or hydroxyl group of β-position; and $R_5$ stands for a hydrogen atom or a hydroxyl group;

A represents a $C_{1-10}$ straight-chain or $C_{3-10}$ branched-chain alkyl group, hydroxy-alkyl, acetyl-alkyl, benzyl, $C_{3-6}$ alkenyl or alkynyl or $C_{5-7}$ cycloalkyl group or an aromatic group or a heteroaromatic group containing one nitrogen or one oxygen atom, or an acetoxyethyl, formylaminoethyl or aminocarbonylethyl group and X stands for oxygen or sulphur atom, as well as their acid addition salts and pharmaceutical preparations containing these compounds.

According to another aspect of the invention, there is provided a process for the preparation of the new compounds of the general formula (I), wherein $R_1$, $R_2$, $R_3$, $R_4$, $R_5$, X and A are the same as defined above, and their acid addition salts, which comprises (a) reacting a compound of the general formula (II),

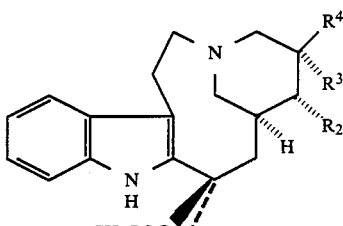

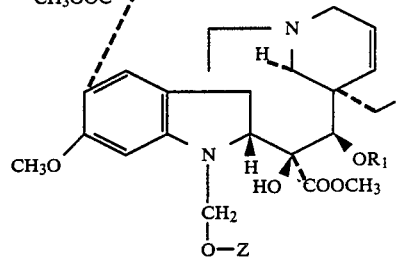

wherein $R_1$, $R_2$, $R_3$ and $R_4$ are the same as defined above and Z represents a leaving group, with a thioalcohol of the general formula (III), $$A-XH \qquad (III)$$

wherein A and X are the same as defined above, in the presence of an acid, preferably in a halogenated hydrocarbon at a temperature below 20° C., then alkalizing by adding a base and isolating the thus-obtained product of the general formula (I), or (b) reacting a compound of the general formula (I), wherein the substituents are the same as defined above, with the proviso that the meaning of A is as defined above but actually different from that of A in the desired product, with a thioalcohol of the general formula (III), wherein the meaning of A and X corresponds to that of A and X in the desired product, in the presence of an acid, preferably in a halogenated hydrocarbon at a temperature below 20° C., then alkalizing by adding a base and isolating the thus-obtained product of the general formula (I), or (c) treating by a simple chemical operation, preferably oxidizing, reducing, deacetylating or acylating, a compound of the general formula (I), wherein the substituents are the same as defined above, whereby the meaning of $R_1$ and $R_5$ is changed, and isolating the thus-obtained product, and, if desired, transforming the thus-obtained product to an acid addition salt thereof.

Substances that are structurally related to the compounds of the invention are reported in the Belgian patent specification No. 889,989. These compounds contain a $-CH_2-OR$ group bound to the $N_1$ atom of the bis-indole skeleton. Both these known compounds as well as novel substances can be used for preparing the compounds of the invention.

The compounds of the general formula (I) show a cytostatic effect with less toxicity than that of the known vinblastine-type bis-indole alkaloid drugs which are commercially available.

For investigating the biological activity, the solutions were prepared by using physiological saline and, if desired in the case of water-insoluble substances, by adding one drop of Tween-80. The injectable solutions were intraperitoneally administered.

The activity of the novel compounds was investigated on intraperitoneally transplantable tumours (P388 mouse leukemic) by using the method described hereinafter.

The P388 leukemic was maintained in DBA/2 inbred mice and transplanted intraperitoneally by administering $10^6$ tumour cells/animal to groups consisting of 6 BDF$_1$ hybrid mice each. In the 24th hour following the transplantation, the treatment with the compounds to be tested was started with daily intraperitoneal injections for 8 days. The body-weight, condition and tumour of the animals were daily observed. The effect achieved on the

TABLE 1

| | | Dose mg/kg i.p. (T/C %) | | | | | |
|---|---|---|---|---|---|---|---|
| Example No. | Chemical structure* | 8 × 0.05 | 8 × 0.1 | 8 × 0.2 | 8 × 0.4 | 8 × 0.7 | 8 × 1 |
| ∅ | VCR | 143–196 | 165–220 | 183–234 | average 167–207 | tox. | — |
| ∅ | VLB | 115 | 165 | average 177–221 | 170 | — | tox. |
| 2 | VLB \N—CH$_2$—S—CH$_2$—CH$_3$ / | — | — | — | 105 | — | 108 |
| 3 | VLB \N—CH$_2$S(CH$_2$)$_6$CH$_3$ / | — | — | — | — | — | — |
| 5. 6. | VLB \N—CH$_2$S—CH$_2$—C$_6$H$_5$ / | | | | 105 | — | 99 |
| 8. | LE \NCH$_2$—S—C$_6$H$_5$ / | — | — | — | — | — | — |
| 10. | LE \NCH$_2$—S—C$_6$H$_5$ / | — | — | — | 106 | — | — |
| 12. | VLB \NCH$_2$—S—(CH$_2$)$_2$OH / | | | | 120 118 | 142 | 163 180 |
| 16 + 17 | LE \NCH$_2$—S(CH$_2$)$_2$OH / | | | | 106 | — | — |
| 14 | VLB \NCH$_2$—S—(CH$_2$)$_2$OAc / | | | | 110 | — | — |
| 13 | 17-desacetyl- VLB \NCH$_2$—S—(CH$_2$)$_2$OH / | | | | 145 139 | — | 135 |

| Example No. | Chemical structure* | 8 × 2 | 8 × 4 | 8 × 8 | 8 × 16 | 1 × 20 | 1 × 40 |
|---|---|---|---|---|---|---|---|
| ∅ | VCR | — | — | — | — | — | — |
| ∅ | VLB | — | — | — | — | — | — |
| 2 | VLB \N—CH$_2$—S—CH$_2$—CH$_3$ / | 100 | 183 | 144 | — | — | — |

TABLE 1-continued

| | | Dose mg/kg i.p. (T/C %) | | | | | |
|---|---|---|---|---|---|---|---|
| 3 | VLB\N—CH₂S(CH₂)₆CH₃/ | — | 108 111 | 115 | 150 | 142 | — |
| 5. 6. | VLB\N—CH₂S—CH₂—C₆H₅/ | 107 | 191 | 171 | 165 | 121 | 124 |
| 8. | LE\NCH₂—S—C₆H₅/ | — | 122 | 135 | — | 121 | — |
| 10. | LE\NCH₂—S—C₆H₅/ | — | 120 | 154 | — | 138 | — |
| 12. | VLB\NCH₂—S—(CH₂)₂OH/ | 209 205 | 263 218 | 215 211 | 172 | 175 | 208 |
| 16 + 17 | LE\NCH₂—S(CH₂)₂OH/ | — | 131 | 158 | 165 | 139 | — |
| 14 | VLB\NCH₂—S—(CH₂)₂OAc/ | 114 | 159 | 152 | — | 119 | — |
| 13 | 17-desacetyl-VLB\NCH₂—S—(CH₂)₂OH/ | 182 170 | 178 | 190 | 215 | 162 | — |

It is obvious from Table 1 that the compounds investigated are capable to extend the survival time of P388 leukemic mice within defined dose limits.

It can be concluded from Table II that the therapeutical index of the compounds of the invention is about 10 to 40 times higher than that of vincristine, i.e. the compounds of the invention are less toxic. The lengthening of the survival time achieved by using the compounds Nos. 1 and 4 is obvious: the effect of these latter compounds is about of the same order as that of vincristine (T/C is higher than 200%), together with a therapeutic index which is more advantageous than that of vincristine.

TABLE II

| Compound | Therapeutic indices |
|---|---|
| Vincristine | 0.4/0.05 = 8 |
| Vinblastine | 0.4/0.1 = 4 |
| No. 1 = N—demethyl-N—(2-hydroxy-ethylthiomethyl)-vinblastine | 8.0/0.7 = 11.4 |
| No. 2 = N—demethyl-N—(2-hydroxy-ethylthiomethyl)-leurosine | 16/4 = 4 |
| No. 3 = N—demethyl-N—(2-acetoxy-ethylthiomethyl)-vinblastine | 8/4 = 2 |
| No. 4 = 17-deacetyl-N—demethyl-N—(2-hydroxyethyl-thiomethyl)-vinblastine | 16/0.4 = 40 |

A preferable property of both above-emphasized compounds is that a high single dose thereof is active, whereas no single dose (including the toxic region, i.e. 1.5 mg/kg) of vincristine can be found which shows an anti-tumour action.

Another advantage of the compounds of the invention is that in the course of and after 8 times repeated administrations of the effective doses, the paralyses of the hind limbs and of the bladder, which are observed on using vincristine and indicate neurotoxic effects, do not appear.

According to a preferred embodiment of the process of the invention, the compounds of the general formula (I) are prepared as follows.

The starting substance of the general formula (II) is reacted with a large excess of the thioalcohol of the general formula (III) by using the process (a) or (b) of the invention. According to the process (b), in case of a defined couple of reactants, the meaning of A and X is always different in the compounds of the general formula (I) and (III), respectively. The thioalcohol of the general formula (III) is suitably used in an amount of 30 to 50 molar equivalents as calculated for the compound of the general formula (II).

The reaction of the compounds of the general formula (II) with the compounds of the general formula (III) is carried out in an organic solvent. Suitable solvents are e.g.: ethers such as ethyl ether, tetrahydrofuran or dioxane; chlorinated hydrocarbons such as dichloromethane, chloroform or carbon tetrachloride; benzene or homologues thereof such as toluene or xylene; or other solvents such as ethyl acetate, acetone or dimethylformamide. An excess of the thioalcohol of the general formula (III) can also be used as solvent. Among the above listed solvents the anhydrous chlorinated hydrocarbons are most preferable.

The reaction is preferably carried out at a pH value of 3 to 5, in the presence of an acid. For adjusting the pH value, particularly mineral acids such as hydrochloric or sulphuric acid or a Lewis acid, e.g. boron trifluoride etherate, may be used.

The temperature of the reaction is selected with the consideration of the melting and boiling points of the selected solvent. The reaction is in general carried out at a temperature between $-60°$ C. and $+25°$ C.

After completion of the reaction, the pH value of the mixture is adjusted to 7 to 9 by adding e.g. ammonium hydroxide or saturated potassium carbonate solution.

The product is obtained from the reaction mixture by extraction and/or evaporation and, if desired, purified by using a chromatographic method and/or recrystallization. The chromatography is performed on a partially deactivated aluminium oxide or on a fine-sized silica gel adsorbent.

According to process (c), a compound of the general formula (I) prepared by using process (a) or (b) is subjected to further transformation. Thus, a 17-deacetyl derivative may be prepared by deacetylation or a 21-hydroxy derivative may be achieved by a mild oxidation or, in turn, a 21-hydroxy derivative may be reformed by reduction. It is evident that particularly the meanings of $R_1$ and $R_5$ in the general formula (I) may be changed by transforming the compounds into each other.

A great part of the compounds of the general formula (II) used as starting substance in the process of the invention are new. These compounds are prepared starting from an N-dimethyl-N-methoxymethylvinblastine or N-demethyl-N-methoxymethylleurosine derivative (wherein X means a methyl group) by a simple transacetalisation. For this purpose ethylene glycol, 1,8-octanediol or other alcohols may be used as reagents.

The compounds of the general formula (II) reported in the Belgian patent specification No. 889,989 mentioned above may also be used as starting substances.

The process variants of the invention are illustrated in detail in the following non-limiting Examples. It should be noted that the target compounds of the invention are described in Examples 1 to 21, whereas the preparation of the hitherto unknown starting substances is reported in Examples 22 to 27.

In Examples 1 to 21, the yields are given as calculated for vinblastine sulphate because a crude product is frequently used as starting material.

EXAMPLE 1

Preparation of
N-demethyl-N-(2-hydroxyethylthiomethyl)-vinblastine

A solution containing 70 mg (0.08 mmole) of N-methoxymethylvinblastine (prepared as described in the Belgian patent specification No. 889,989) and 0.5 ml (7.5 mmoles) of 2-mercaptoethanol in 3 ml of dichloromethane is acidified at 0° C. to pH 3 by adding abs. ethereal hydrogen chloride solution. The course of the reaction is followed by thin layer chromatography (TLC) (by using a silica gel sheet and a developing system containing dichloromethane and methanol in a ratio of 20:3; the $R_f$ value of the aimed product is lower than that of the starting substance). At the end point of the reaction, i.e. after 5 minutes at 0° C., the solution is diluted by adding 15 ml of abs. ether. A white precipitate is separated which is filtered by suction and washed first with 3 ml of abs. ether and then with 3 ml of pentane to give the hydrochloride of the aimed product in a yield of 65 mg (83%), in analytical purity. This product may be recrystallized from a cold mixture of abs. dimethyl formamide and ether. The hydrochloride is readily soluble in water and does not show a characteristic melting point (decomposition).

EXAMPLE 2

Preparation of
N-demethyl-N-ethylthiomethylvinblastine

A solution containing 0.80 g of crude N-demethyl-N-methoxymethyl-vinblastine (prepared as described in the Belgian patent specification No. 889,989) and 1.7 ml (23 mmoles) of ethyl mercaptan in 40 ml of abs. dichloromethane is acidified to pH 3 by adding abs. ethereal hydrogen chloride solution at 0° C., whereupon the mixture is stirred for additional 10 minutes. The course of the reaction is followed by TLC (by using a developing system containing dichloromethane and methanol in a ratio of 20:2; the $R_f$ value of the aimed product is higher than that of the starting substance). At the end point of the reaction, the hydrochloride of the aimed product begins to precipitate. The separation of the salt is completed by adding 50 ml of abs. ether and 20 ml of petroleum ether. The precipitate is filtered and washed twice with 10 ml of a 2:1 mixture of ether and petroleum ether each and dried under reduced pressure. In order to liberate the base, the hydrochloride is dissolved in 15 ml of water, the pH value of the solution is adjusted to 9.5 by adding concentrated ammonium hydroxide solution and extracted 4 times with 20 ml of dichloromethane each. The organic solution is washed twice with 5 ml of water each, dried and evaporated under reduced pressure to give 0.72 g of a crude product which is subjected to column chromatography on 20 g of a silica gel adsorbent (particle size 0.04 to 0.063 mm). The product is applied to the column in a dichloromethane solution and developed with 100 ml of dichloromethane. The elution is carried out first with dichloromethane containing 1% of methanol and then with dichloromethane containing 2% of methanol. The first 150 to 200 ml portion of the eluate does not contain any product.

By using the above method, 490 mg (52%) of the aimed product are obtained. After suspending the adsorbent column with 80 ml of methanol, filtering, evaporating and purifying the residue by TLC (by using Merck silica gel $PF_{254+366}$ and a developing system containing ether, diethylamine, benzene and ethanol in a ratio of 100:5:5:5), 60 mg of vincristine and 20 mg of N-demethylvinblastine can also be obtained.

The characteristics of the aimed product are as follows:

m.p.: 194°–196° C. (amorphous); $[\alpha]_D + 26°$ (c=1, chloroform); $[\alpha]_{546} = +35°$ (c=1, chloroform).

Empirical formula: $C_{48}H_{62}N_4O_9S$.

IR (KBr, $cm^{-1}$): 730, 870, 1020, 1120, 1200–1240, 1365, 1450, 1495, 1605, 1730, 2900, 3400.

EXAMPLE 3

Preparation of N-demethyl-N-heptylthiomethylvinblastine

A solution containing 0.80 g of crude N-demethyl-N-methoxymethylvinblastine and 3.5 ml (23 mmoles) of heptyl mercaptan in 40 ml of dichloromethane is acidified to pH 3 by adding abs. ethereal hydrogen chloride solution at 0° C., then the mixture is stirred at the same temperature for 10 minutes and at room temperature for 10 minutes. The course of the reaction is followed by TLC (by using a developing system containing dichloromethane and methanol in a ratio of 20:2; the $R_f$ value of the product is higher than that of the starting substance). After adding 50 ml of abs. ether and 20 ml of petroleum ether, the hydrochloride of the reaction product is precipitated from the mixture, and after filtration this product is washed with 20 ml of a 2:1 mixture of ether and petroleum ether. The air-dried salt is dissolved in 15 ml of water, alkalized to a pH value of 9.5 by adding concentrated ammonium hydroxide solution and the oily base is extracted 4 times with 20 ml of dichloromethane each. The combined organic solution is washed twice with 5 ml of water each, dried and evaporated to give 0.74 g of a crude product which is subjected to column chromatography on 20 g of a silica gel adsorbent (particle size 0.04 to 0.063 mm). The product is applied to the column in 15 ml of dichloromethane and developed by using 100 ml of dichloromethane. The elution is carried out first with 100 ml of dichloromethane containing 1% of methanol and then with 250 ml of dichloromethane containing 2% of methanol. The fraction containing vincristine and N-demethylvinblastine remaining on the column is washed out with 70 ml of methanol. The first 200 ml portion of the eluate is free of any substance.

From the fraction containing 2% of methanol, the aimed product is obtained in a yield of 490 mg (47%), whereas 70 mg of vincristine and 15 mg of N-demethylvinblastine are obtained from the column residue by using TLC separation (by means of silica gel $PF_{254+366}$ and a developing system consisting of ether, diethyl amine, benzene and ethanol in a ratio of 100:5:5:5).

The characteristics of the aimed product are as follows: amorphous; m.p.: 225°–226° C. (with decomposition); $[\alpha]_D = +41°$ (c=1, chloroform); $[\alpha]_{546} = +57°$ (c=1, chloroform).

Empirical formula: $C_{53}H_{72}N_4O_9S$.

IR (KBr, cm$^{-1}$): 730, 1020, 1125, 1220, 1240, 1370, 1435, 1460, 1495, 1610, 1745, 2900, 3400.

EXAMPLE 4

Preparation of 17-deacetyl-N-demethyl-N-heptylthiomethylvinblastine

A solution containing 120 mg (0.12 mmole) of N-heptylthiomethylvinblastine in 7 ml of a 0.5N sodium methoxide solution is allowed to stand at room temperature and the course of the reaction is observed by TLC (by means of a developing system containing dichloromethane and methanol in a ratio of 20:2; the $R_f$ value of the product is lower than that of the starting substance). After 24 hours, the base is neutralized by adding the equivalent (0.21 ml) of glacial acetic acid, the solution is evaporated under reduced pressure, then the residue is dissolved in 25 ml of dichloromethane and extracted at a pH value of 9.5 (which is adjusted by adding a 1:1 ammonium hydroxide solution). The organic phase is washed twice with 3 ml of water each, dried and evaporated to give 110 mg of a crude product which is purified by column chromatography on a silica gel adsorbent (particle size 0.04 to 0.063 mm). The product is dissolved in 20 ml of dichloromethane and the elution is carried out first with 100 ml of dichloromethane containing 1% of methanol, then with 200 ml of dichloromethane containing 3% of methanol and finally with 300 ml of dichloromethane containing 5% of methanol to give the aimed product in a yield of 87 mg (76%); amorphous; m.p.: 145°–147° C. (with decomposition); $[\alpha]_D = +47°$ (c=1.04, chloroform); $[\alpha]_{546} = +66$ (c=1.04, chloroform).

Empirical formula: $C_{51}H_{70}N_4O_8S$.

IR (KBr, cm$^{-1}$): 740, 900, 1030, 1135, 1205–1240, 1440, 1465, 1500, 1615, 1730, 2950, 3400.

EXAMPLE 5

Preparation of N-demethyl-N-benzylthiomethylvinblastine

A solution containing 0.80 g of crude N-demethyl-N-methoxymethylvinblastine and 2.8 ml (23 mmoles) of benzyl mercaptan in 40 ml of dichloromethane is acidified to pH 3 by adding abs. ethereal hydrogen chloride solution at 0° C., then the reaction mixture is stirred at the same temperature for additional 10 minutes. The trans-acetalisation reaction is followed by TLC (by using a developing system containing dichloromethane and methanol in a ratio of 20:2; the $R_f$ value of the product is higher than that of the starting substance). The hydrochloride of the aimed product begins to separate in a short time and completed by adding 50 ml of abs. ether and 20 ml of petroleum ether. The precipitate is filtered by suction, washed with 20 ml of a 2:1 mixture containing ether and petroleum ether and dried under reduced pressure. The thus-obtained salt is suspended in 10 ml of water, alkalized to pH 9 by adding concentrated ammonium hydroxide solution and the separated base is extracted 4 times with 20 ml of dichloromethane each. The combined organic phase is washed twice with 5 ml of water each, dried and evaporated to give 0.70 g of a crude base which is purified on 20 g of a silica gel adsorbent (particle size 0.04 to 0.063 mm). The product is applied to the column as dissolved in 15 ml of dichloromethane and developed with 100 ml of dichloromethane. The elution is carried out first with 100 ml of dichloromethane containing 1% of methanol, then with 250 ml of dichloromethane containing 2% of methanol. The first 150 to 200 ml portion of the eluate is free from any substance.

By using the above method, 480 mg (47%) of the aimed product are obtained. The fraction containing vincristine and N-demethylvinblastine is not eluted but the adsorbent column is suspended in 70 ml of methanol, filtered and evaporated. The thus-obtained substance weighing 110 mg is purified by TLC (by using silica gel $PF_{254+366}$ and a developing system containing ether, diethyl amine, benzene and ethanol in a ratio of 100:5:5:5) to give 50 mg of vincristine and 30 mg of N-demethylvinblastine.

The characteristics of the aimed product are as follows:

M.p.: 176°–178° C. (with decomposition); amorphous; $[\alpha]_D = +87°$ (c=1, chloroform; $[\alpha]_{546} = +105°$ (c=1, chloroform).

Empirical formula: $C_{53}H_{64}N_4O_9S$.

IR (KBr, cm$^{-1}$): 730, 1015, 1120, 1200–1240, 1360, 1450, 1490, 1605, 1730, 2900, 3400.

EXAMPLE 6

Preparation of N-demethyl-N-benzylthiomethylvinblastine from N-demethyl-N-heptylthiomethylvinblastine [by using process (b)]

A solution containing 10 ml (0.01 mmole) of N-demethyl-N-heptylthiomethylvinblastine and 0.05 ml (40 mmoles) of benzyl mercaptan in 3 ml of abs. dichloromethane is acidified to pH 2 by adding abs. ethereal hydrogen chloride solution at 0° C. The trans-acetalisation is followed by TLC (by using a developing system containing dichloromethane and methanol in a ratio of 20:2; the $R_f$ value of the product is lower than that of the starting substance). After 24 hours, the precipitated hydrochloride is brought into solution by adding one drop of methanol, the mixture is diluted with 3 ml of dichloromethane, then the acid is neutralized by adding 2 ml of a solution containing concentrated ammonium hydroxide and water in a 1:1 ratio. The organic phase is washed twice with 2 ml of water each, dried and evaporated to give 8 mg of N-demethyl-N-benzylthiomethylvinblastine.

EXAMPLE 7

Preparation of N-demethyl-N-phenylthiomethylleurosine and N-demethyl-21'-hydroxy-N-phenylthiomethylleurosine A solution containing 1.2 g of crude N-demethyl-N-methoxymethylleurosine (prepared from leurosine sulphate) and 4 ml of thiophenol in 50 ml of abs. dichloromethane is acidified to pH 2 by portionwise adding abs. ethereal hydrogen chloride solution at 0° C. under vigorous stirring. The course of the reaction is followed by TLC (by using a developing system containing dichloromethane and methanol in a ratio of 20:2; the $R_f$ values of the products are higher than that of the starting substance). At the end point of the reaction, i.e. after about 30 minutes at 0° C., the hydrochlorides of the aimed products are precipitated by adding 100 ml of a 1:1 mixture of ether and petroleum ether, whereupon the excess reagent is washed out by using the above solvent mixture. The air-dried salt is dissolved in 15 ml of water, alkalized to pH 8 by adding concentrated ammonium hydroxide solution and the base is extracted 4 times with 20 ml of dichloromethane each. The combined organic phase is washed twice with 15 ml of water each, dried and evaporated under reduced pressure. The thus-obtained product is purified by column chromatography.

By using the above method, 210 mg (14%) of N-demethyl-21'-hydroxy-N-phenylthiomethylleurosine and 440 mg (29%) of N-demethyl-N-phenylthiomethylleurosine are obtained. These yields are given as calculated for leurosine sulphate. The repeated purification of the separated materials can be achieved by an additional chromatographic treatment.

The characteristics of N-demethyl-21'-hydroxy-N-phenylthiomethylleurosien are as follows:

M.p.: 189°–192° C. (with decomposition); amorphous; $[\alpha]_D = +106°$ (c=1, chloroform); $[\alpha]_{546} = +141°$ (c=1, chloroform).

Empirical formula: $C_{52}H_{60}N_4O_{10}S$.

IR (KBr, cm$^{-1}$): 690, 730, 810, 980, 1020, 1200–1260, 1370, 1435, 1495, 1605, 1730, 2850, 3350–3450.

The characteristics of N-demethyl-N-phenylthiomethylleurosine are as follows:

M.p.: 178°–180° C. (with decomposition); amorphous; $[\alpha]_D = +96°$ (c=1, chloroform); $[\alpha]_{546} = +122°$ (c=1, chloroform).

Empirical formula: $C_{52}H_{60}N_4O_9S$.

IR (KBr, cm$^{-1}$): 690, 740, 805, 890, 930, 1020, 1200–1240, 1370, 1455, 1495, 1605, 1730, 2850, 3400.

EXAMPLE 8

Preparation of N-demethyl-N-phenylthiomethylleurosine from N-demethyl-21'-hydroxy-N-phenylthiomethylleurosine Sodium borohydride is added in small portions at 0° C. to a solution containing 10 mg of the 21'-hydroxy derivative in 2 ml of methanol under vigorous stirring. The course of the reaction is observed by TLC (by using a developing system containing dichloromethane and methanol in a ratio of 20:2; the $R_f$ value of the aimed product is lower than that of the starting substance). The excess of the reducing agent is decomposed by adding one drop of glacial acetic acid, then the solution is evaporated under reduced pressure. The residue is dissolved in 20 ml of dichloromethane, alkalized to pH 9 by adding concentrated ammonium hydroxide and then extracted. The organic phase is washed twice with 3 ml of water each, dried over anhydrous magnesium sulphate and evaporated to give the aimed product in a yield of 7 mg.

EXAMPLE 9

Preparation of 17-deacetyl-N-demethyl-N-phenylthiomethylleurosine

A mixture containing 30 mg of N-demethyl-N-phenylthiomethylleurosine in 3 ml of 0.5N sodium methoxide solution is allowed to stand at room temperature. The course of the reaction is followed by TLC (by using a developing system containing dichloromethane and methanol in a ratio of 20:2; the $R_f$ value of the product is lower than that of the starting substance): After 24 hours, the base is neutralized by adding an equivalent amount (0.09 ml) of glacial acetic acid and the mixture is evaporated under reduced pressure. The residue is dissolved in 30 ml of dichloromethane, washed first with 3 ml of saturated potassium carbonate solution, then twice with 3 ml of water each, dried over anhydrous magnesium sulphate and evaporated under reduced pressure. The thus-obtained crude product is purified by column chromatography to give the aimed product in a yield of 17.6 mg (61.5%); m.p.: 170°–172° C. (with decomposition); amorphous; $[\alpha]_D = +131°$ (c=0.35, chloroform); $[\alpha]_{546} = +165°$ (c=0.35, chloroform).

Empirical formula: $C_{50}H_{58}N_4O_8S$.

IR (KBr, cm$^{-1}$): 740, 805, 900, 1015, 1210–1260, 1460, 1500, 1610, 1730, 2900, 3400.

EXAMPLE 10

Preparation of N-demethyl-N-(2-pyridylthiomethyl)-leurosine and N-demethyl-21'-hydroxy-N-(2-pyridylthiomethyl)-leurosine A solution containing 1.1 g of crude N-demethyl-N-methoxymethylleurosine and 1.8 g of 2-mercaptopyridine in 70 ml of abs. dichloromethane is acidified at 0° C. to pH 2 by the portionwise addition of abs. ethereal hydrogen chloride solution under vigorous stirring. The trans-acetalisation is followed by TLC (by using a developing system containing dichloromethane and methanol in a ratio of 20:1; the $R_f$ values of the products are higher than that of the starting material after repeated development). At the end point of the reaction, i.e. after about 60 minutes at 0° C., the hydrogen chloride is neutralized by adding 20 ml of saturated potassium carbonate solution, the phases are separated and the aqueous layer is extracted twice with 20 ml of dichloromethane each. The combined organic phase is washed 5 times with 10 ml of water each, dried over anhydrous magnesium sulphate and evaporated under reduced pressure. The crude product is purified by column chromatography on a silica gel adsorbent, by using dichloromethane containing 1 to 3% of methanol as eluent. In this way, 120 mg (9.5%) of N-demethyl-21'-hydroxy-N-(2-pyridylthiomethyl)-leurosine and 260 mg (20%) of N-demethyl-N-(2-pyridylthiomethyl)-leurosine are obtained.

The characterics of N-demethyl-21'-hydroxy-N-(2-pyridylthiomethyl)-leurosine are as follows M.p.: 188°–192° C. (amorphous); $[\alpha]_D = +151°$ (c=1, chloroform); $[\alpha]_{546} = +194°$ (c=1, chloroform).

Empirical formula: $C_{51}H_{59}N_5O_{10}S$.

IR (KBr, $cm^{-1}$): 740, 830, 1030, 1105, 1200–1240, 1370, 1455, 1495, 1570, 1605, 1730, 2850, 3350.

The characteristics of N-demethyl-N-(2-pyridylthiomethyl)-leurosine are as follows:

M.p.: 210° C. (with decomposition); amorphous; $[\alpha]_D = +119°$ (c=1, chloroform); $[\alpha]_{546} = +156°$ (c=1, chloroform).

Empirical formula: $C_{51}H_{59}N_5O_9S$.

IR (KBr, $cm^{-1}$): 740, 1035, 1120, 1220–1260, 1380, 1470, 1505, 1595, 1620, 1740, 2950, 3450.

EXAMPLE 11

Preparation of N-demethyl-N-(2-hydroxyethylthiomethyl)-vinblastine

After adding 4 ml (56 mmoles) of 2-mercaptoethanol to a solution containing 1.6 g of crude N-demethyl-N-methoxymethylvinblastine in 120 ml of abs. dichloromethane, the mixture is cooled to 0° C. and the pH value is adjusted to 2 by the portionwise addition of abs. ethereal hydrogen chloride solution under vigorous stirring. The course of the reaction is followed by TLC (by using a developing system containing dichloromethane and methanol in a ratio of 20:2; the $R_f$ value of the product is lower than that of the starting substance). At the end point of the reaction (in general after 30 minutes at 0° C.), the acid is neutralized by adding 20 ml of saturated potassium carbonate solution, and after separating the phases, the aqueous solution is extracted 3 times with 20 ml of dichloromethane each. The combined organic phase is washed twice with 15 ml of water each, dried over anhydrous magnesium sulphate and evaporated under reduced pressure. The excess of the reagent is removed by thoroughly triturating the thus-obtained oily product 3 times with 20 ml of petroleum ether each. The thus-obtained substance is dried under reduced pressure and then purified by column chromatography under the following conditions.

Adsorbent: silica gel with a particle size of 0.04–0.063 mm

Column: 30 mm in diameter, 120 mm in height; in dichloromethane.

Dissolving and washing: dichloromethane, 20+50 ml.

Development: with 100 ml of dichloromethane.

Elution:
- with 200 ml of a mixture containing 1% of methanol in dichloromethane;
- with 200 ml of a mixture containing 3% of methanol in dichloromethane;
- with 600 ml of a mixture containing 5% of methanol in dichloromethane;
- with 600 ml of a mixture containing 7% of methanol in dichloromethane; and
- with 200 ml of a mixture containing 10% of methanol in dichloromethane.

TLC: with a developing system containing dichloromethane and methanol in a 20:2 ratio.

In general, the thioether can be eluted by dichloromethane containing 5 to 7% of methanol.

In this way 70 mg of an impure and 800 mg (41%) of pure product are obtained which can be made free from the beige colouring materials by repeated chromatography on an aluminium oxide adsorbent.

The characteristics of the aimed product are as follows:

M.p.: 198°–200° C. (with decomposition); amorphous; $[\alpha]_D = +21°$ (c=1, chloroform); $[\alpha]_{546} = +28°$ (c=1, chloroform).

Empirical formula: $C_{48}H_{62}N_4O_{10}S$.

IR (KBr, $cm^{-1}$): 740, 1020, 1210–1260, 1360, 1450, 1490, 1600, 1720, 2900, 3200–3400.

EXAMPLE 12

Preparation of N-demethyl-N-(2-hydroxyethylthiomethyl)-vinblastine from N-demethyl-N-(2-hydroxyethyloxymethyl)-vinblastine

Method (a)

A solution containing 10 mg (0.01 mmole) of N-demethyl-N-(2-hydroxyethyloxymethyl)-vinblastine and 0.05 ml (0.64 mmole) of 2-mercaptoethanol in 5 ml of dichloromethane is acidified to pH 3 by adding abs. ethereal hydrogen chloride solution at 0° C. The reaction mixture is stirred for 5 minutes, while the course of the reaction is observed by TLC (by using a developing system containing dichloromethane and methanol in a ratio of 20:2; the $R_f$ value of the product is higher than that of the starting substance), then the acid is neutralized with 1.5 ml saturated potassium carbonate solution. The organic phase is washed twice with 1.5 ml of water each, dried over anhydrous magnesium sulphate and evaporated. The thus-obtained product is purified by preparative layer chromatography (by using silica gel $PF_{254+366}$ with a developing system containing dichloromethane and methanol in a ratio of 100:10). In this way 7 mg of the aimed product are obtained, all characteristics of which are identical with those of a product prepared by an authentic method.

Method (b)

Method (a) is followed with the same amounts of the starting substances, except that 10 μl of boron trifluoride etherate are used as catalyst. The reaction lasts 5 minutes at 0° C. to give a yield of 6.5 mg.

EXAMPLE 13

Preparation of 17-deacetyl-N-demethyl-N-(2-hydroxyethylthiomethyl)-vinblastine

A mixture containing 800 mg (0.9 mmole) of N-demethyl-N-(2-hydroxyethylthiomethyl)-vinblastine in 90 ml of 0.5N sodium methoxide solution is allowed to stand at room temperature. The course of the reaction is followed by TLC (by using a developing system containing dichloromethane and methanol in a ratio of 20:2; the $R_f$ value of the product is lower than that of the starting substance). The base is neutralized by adding 2.7 ml, i.e. an equivalent amount of glacial acetic acid, then the mixture is evaporated. The residue is dissolved in 100 ml of dichloromethane, washed with 20 ml of saturated potassium carbonate solution, then the aqueous phase is extracted twice with 15 ml of dichloromethane each. The combined organic phase is washed twice with 15 ml of water each, dried over anhydrous magnesium sulphate and evaporated under reduced pressure. The thus-obtained crude product is purified by column chromatography.

By using the above method, the aimed product is obtained in a yield of 0.54 g (72%); m.p: 198°-202° C. (with decomposition) after recrystallization from methanol; amorphous; $[\alpha]_D = +44°$ (c=1, chloroform); $[\alpha]_{546} = +58°$ (c=1, chloroform).

Empirical formula: $C_{46}H_{60}N_4O_9S$.

IR (KBr, $cm^{-1}$): 740, 1030, 1140, 1220, 1260, 1440, 1460, 1500, 1610, 1725, 2900, 3400.

EXAMPLE 14

Preparation of N-demethyl-N-(2-acetoxyethylthiomethyl)-vinblastine

A solution containing 100 mg (0.11 mmole) of N-demethyl-N-(2-hydroxyethylthiomethyl)-vinblastine and 0.5 ml of acetic anhydride in 1.5 ml of abs. pyridine is allowed to stand at room temperature. In general, the reaction lasts 3 hours; the course of the reaction is controlled by TLC (by using a developing system containing dichloromethane and methanol in a ratio of 20:2; the $R_f$ value of the product is higher than that of the starting substance). Then the solution is poured into 3 ml of ice-water, the pH value is adjusted to 9.5 by adding ammonium hydroxide solution and the oily precipitate is extracted 3 times with 20 ml of dichloromethane each. The combined organic solution is washed twice with 10 ml of water each, dried and evaporated under reduced pressure. The residue pyridine is removed by triturating 3 times with 15 ml of petroleum ether each and the thus-obtained crude product is purified by column chromatography.

By using the above method, the aimed product is obtained in a yield of 65 mg (63%); m.p.: 168°-170° C. (amorphous); $[\alpha]_D = +30°$ (c=1, chloroform); $[\alpha]_{546} = +38°$ (c=1, chloroform).

Empirical formula: $C_{50}H_{64}N_4O_{11}S$.

IR (KBr, $cm^{-1}$): 735, 795, 830, 1120, 1130, 1200-1260, 1370, 1435, 1460, 1495, 1610, 1720-1740, 2920, 3450.

EXAMPLE 15

Preparation of N-demethyl-21'-hydroxy-N-(2-hydroxyethylthiomethyl)-leurosine and N-demethyl-N-(2-hydroxyethylthiomethyl)-leurosine A mixture containing 1.6 g of crude N-demethyl-N-methoxymethylleurosine and 3.8 ml of 2-mercaptoethanol in 100 ml of abs. dichloromethane is acidified to pH 2 by the portionwise addition of abs. ethereal hydrogen chloride solution at 0° C. while vigorous stirring. The course of the reaction is followed by TLC (by using a developing system containing dichloromethane and methanol in a ratio of 20:2; the $R_f$ value of the product is lower than that of the starting substance). At the end point of the reaction, 100 ml of an 1:1 mixture of ether and petroleum ether are added to the solution, the precipitated salt is filtered and washed with the above solvent mixture. The air-dried salt is dissolved in 20 ml of water, alkalized to a pH value of 9.5 by adding ammonium hydroxide solution and the separated oily base is extracted 5 times with 20 ml of dichloromethane each. The combined organic solution is washed twice with 20 ml of water each, dried over anhydrous magnesium sulphate and evaporated under reduced pressure to give 1.4 g of a crude product which is purified by column chromatography.

By using the above method, 200 mg (10%) of the 21'-hydroxy-thioether derivative and 700 mg (36%) of the thioether derivative are obtained. Both products are of about 85% purity, and are subjected to a repeated chromatographic treatment for purification.

In this way N-demethyl-21'-hydroxy-N-(2-hydroxyethylthiomethyl)-leurosine is obtained in a yield of 120 mg; m.p.: 128°-135° C. (with decomposition); amorphous; $[\alpha]_D = +30°$ (c=0.8, chloroform); $[\alpha]_{546} = +40°$ (c=0.8, chloroform).

Empirical formula: $C_{48}H_{60}N_4O_{11}S$.

IR (KBr, $cm^{-1}$): 730, 880, 925, 1020, 1040, 1130, 1220-1260, 1325, 1360, 1460, 1495, 1605, 1720, 2900, 3300-3500.

Thioether fraction

Adsorbent: aluminium oxide II-III.
Column: 20 mm in diameter, 140 mm in height; in dichloromethane.
Dissolving and washing: dichloromethane, 20+80 ml.
Development:
  with 250 ml of dichloromethane containing 0.5% of methanol; and
  with 400 ml of dichloromethane containing 1% of methanol (giving the thioether derivative).
TLC: with a developing system containing dichloromethane and methanol in a 20:2.5 ratio.

In this way N-demethyl-N-(2-hydroxyethylthiomethyl)-leurosine is obtained in a yield of 600 mg; m.p.: 201°-203° C. (with decomposition); $[\alpha]_D = +48°$ (c=1, chloroform); $[\alpha]_{546} = +64°$ (c=1 chloroform).

Empirical formula: $C_{48}H_{60}N_4O_{10}S$.

IR (KBr, $cm^{-1}$): 740, 1030, 1040, 1140, 1200-1260, 1340, 1380, 1470, 1505, 1620, 1740, 2950, 3450.

EXAMPLE 16

Preparation of
N-demethyl-N-(2-hydroxyethylthiomethyl)-leurosine
from N-demethyl-N-phenylthiomethylleurosine [by using process (b)]

A solution containing 20 mg of N-demethyl-N-phenylthiomethylleurosine and 0.4 ml of 2-mercaptoethanol in 30 ml of abs. dichloromethane is cooled to 0° C. and acidified to pH 2 by adding abs. ethereal hydrogen chloride solution at 0° C. The course of the reaction is followed by TLC (by using a developing system containing dichloromethane and methanol in a ratio of 20:1 with repeated development). At the end point of the reaction (i.e. after about 20 minutes at 0° C.), the acid is neutralized by adding 10 ml of saturated potassium carbonate solution. After separation of the phases, the aqueous layer is extracted twice with 10 ml of dichloromethane each. The combined organic solution is washed twice with 14 ml of water each, dried and evaporated under reduced pressure. The excess of the reagent is removed from the oily residue by triturating twice with 10 ml of petroleum ether each and thus-obtained crude product is purified by preparative layer chromatography (PLC) (by using silica gel $PF_{254+366}$ and a developing system containing dichloromethane and methanol in a ratio of 100:5 with repeated development). In this way the aimed product is obtained in a yield of 15 mg. The characteristics of this substance are identical with those of the previously prepared product.

EXAMPLE 17

Preparation of
N-demethyl-N-(2-hydroxyethylthiomethyl)-leurosine
from
N-demethyl-21'-hydroxy-N-(2-hydroxyethylthiomethyl)-leurosine [by using process (c)]

Sodium borohydride is portionwise added at 0° C. to a solution containing 10 mg of the 21'-hydroxy derivative in 3 ml of methanol. The reaction lasts about 10 minutes; it is followed by TLC (by using a developing system containing dichloromethane and methanol in a ratio of 20:2; the $R_f$ value of the product is lower than that of the starting substance). At the end point of the reaction, the excess of the reducing agent is decomposed by one drop of glacial acetic acid, then the mixture is evaporated under reduced pressure. The residue is dissolved in 10 ml of dichloromethane, washed with 2 ml of saturated potassium carbonate solution and then twice with 2 ml of water each, dried over anhydrous magnesium sulphate and evaporated to give 7 mg of the aimed product.

EXAMPLE 18

Preparation of
N-demethyl-N-furfurylthiomethylvinblastine

A solution containing 250 mg of N-methoxymethyl-vinblastine and 1.7 ml (14.5 mmoles) of furfuryl mercaptan in 20 ml of abs. dichloromethane is acidified to pH 2 by adding abs. ethereal hydrogen chloride solution. After some minutes, a salt begins to precipitate which is completed by adding 20 ml of ether and 20 ml of petroleum ether. The salt is filtered out, washed with the same solvent mixture, then suspended in 15 ml of water, alkalized to pH 9 and extracted into dichloromethane. The aimed product is obtained in a yield of 230 mg (84%).

IR (KBr, $cm^{-1}$): 730, 930, 1020, 1210–1250, 1370, 1460, 1495, 1605, 1730, 2950, 3430.

EXAMPLE 19

Preparation of
N-demethyl-N-(2-hydroxyethyloxymethyl)-vinblastine

After adding 2 ml of ethylene glycol to a solution containing 1.6 g of crude N-demethyl-N-methoxymethylvinblastine in 70 ml of abs. dichloromethane at 0° C., the mixture is acidified to a pH value of 2 to 3 by adding abs. ethereal hydrogen chloride solution while vigorous stirring. The trans-acetalisation is followed by TLC (by using a developing system containing dichloromethane and methanol in a ratio of 203; the $R_f$ value of the product is lower than that of the starting substance). During acidification a dark red oil separates from the mixture.

At the end point of the reaction (i.e. after 20 minutes at 0° C.), the acid is neutralized by adding 20 ml of saturated potassium carbonate solution, then alkalized to pH 9.5 by adding concentrated ammonium hydroxide solution and the aqueous phase is extracted twice with 20 ml of dichloromethane each. The combined organic solution is washed twice with 15 ml of water each, dried over anhydrous magnesium sulphate and evaporated under reduced pressure to give 1.6 g of an oily product which is purified by column chromatography. In this way 280 mg of pure and 80 mg of a slightly impure aimed product are obtained, m.p.: 228°–230° C. (with decomposition); amorphous; $[\alpha]_D = +28°$ (c=1, chloroform); $[\alpha]_{546} = +40°$ (c=1, chloroform).

Empirical formula: $C_{48}H_{62}N_4O_{11}$.

IR (KBr, $cm^{-1}$): 730, 1030, 1100, 1200–1240, 1370, 1460, 1495, 1605, 1730, 2900, 3400.

EXAMPLE 20

Preparation of
N-demethyl-21'-hydroxy-N-(2-hydroxyethyloxymethyl)-leurosine and
N-demethyl-N-(2-hydroxyethyloxymethyl)-leurosine A solution containing 1.6 g of crude N-demethyl-N-methoxymethylleurosine in 100 ml of dichloromethane and 1.4 ml of ethylene glycol is acidified to a pH value of 2 to 3 by the portionwise addition of abs. ethereal hydrogen chloride solution at 0° C. while vigorous stirring. In the course of the reaction a red oil separates in the form of an emulsion. The trans-acetalisation is followed by TLC (by using a developing system containing dichloromethane and methanol in a ratio of 20:3; the $R_f$ value of the product is lower than that of the starting substance). The reaction commonly lasts 10 to 20 minutes at 0° C. At the end point of the reaction, the acid is neutralized by adding 20 ml of a saturated potassium carbonate solution and the aqueous layer is extracted twice with 15 ml of dichloromethane each. The combined organic solution is washed twice with 15 ml of water each, dried over anhydrous magnesium sulphate and evaporated under reduced pressure to give 1.4 g of an oily product which is purified by column chromatography.

By using the above method, 50 mg (2.6%) of 21'-hydroxy derivative and 700 mg (37%) of N-demethyl-N-(2-hydroxyethyloxymethyl)-leurosine are obtained; the latter product is further purified by a repeated chromatographic treatment.

The characteristics of N-demethyl-21'-hydroxy-N-(2-hydroxyethyloxymethyl)-leurosine are as follows:

Empirical formula: $C_{48}H_{60}N_4O_{12}$.

IR (KBr, $cm^{-1}$): 745, 1040, 1220–1260, 1380, 1470, 1505, 1620, 1740, 2950 and 3400.

N-demethyl-N-(2-hydroxyethyloxymethyl)-leurosine:

In this way 500 mg of pure product and 80 mg of a substance of 85% purity are obtained; m.p.: 215°–217° C. (with decomposition); amorphous; $[\alpha]_D = +55°$ (c=1, chloroform); $[\alpha]_{546} = +75°$ (c=1, chloroform).

Empirical formula: $C_{48}H_{60}N_4O_{11}$.

IR (KBr, $cm^{-1}$): 730, 820, 1020, 1200–1240, 1320, 1360, 1450, 1495, 1600, 1720, 2900, 3300–3400.

EXAMPLE 21

Preparation of 17-deacetyl-N-demethyl-N-(2-hydroxyethyloxymethyl)-leurosine

A mixture containing 150 mg (0.17 mmole) of N-demethyl-N-(2-hydroxyethyloxymethyl)-leurosine in 5 ml of 0.5N sodium methoxide solution is allowed to stand at room temperature for 24 hours. The course of the reaction is followed by TLC (by using a developing system containing dichloromethane and methanol in a ratio of 20:2; the $R_f$ value of the product is lower than that of the starting substance). The base is neutralized with 0.15 ml (i.e. with the equivalent amount) of glacial acetic acid, then the solution is evaporated under reduced pressure. The residue is dissolved in 50 ml of dichloromethane, washed with 15 ml of saturated potassium carbonate solution and then twice with 10 ml of water each, dried over anhydrous magnesium sulphate and evaporated under reduced pressure. The thus-obtained crude product is purified by column chromatography to give the aimed product in a yield of 85 mg; m.p.: 180°–191° C. (with decomposition); amorphous, $[\alpha]_D = +68°$ (c=0.8, chloroform); $[\alpha]_{546} = +90°$ (c=0.8, chloroform).

Empirical formula: $C_{46}H_{58}N_4O_{10}$.

IR (KBr, $cm^{-1}$): 750, 1040, 1220, 1470, 1510, 1620, 1730, 2950, 3450.

EXAMPLE 22

Preparation of N-demethyl-N-(2-acetoxyethyloxymethyl)-leurosine

A solution containing 150 mg of N-demethyl-N-(2-hydroxyethyloxymethyl)-leurosine in 2.5 ml of abs. pyridine is treated with 0.5 ml of acetic anhydride at room temperature. The acetylation is followed by TLC (by using a developing system containing dichloromethane and methanol in a ratio of 20:2; the $R_f$ value of the product is higher than that of the starting substance). At the end point of the reaction (i.e. after 4 hours at 25° C.), the solvent is distilled off at 40° C. under a pressure of 1.5 Hgmm, the residue is dissolved in 40 ml of dichloromethane, the pH value of the mixture is adjusted to 9.5, by adding concentrated ammonium hydroxide solution, and extracted. The organic phase is washed twice with 15 ml of water each, dried over magnesium sulphate and evaporated. The last traces of pyridine are removed by triturating twice with 15 ml of petroleum ether each to give 100 mg of a crude product which is purified by column chromatography. In this way the aimed product is obtained in a yield of 58 mg (37%); m.p.: 168°–170° C. (with decomposition); amorphous; $[\alpha]_D = +41°$ (c=0.65, chloroform); $[\alpha]_{546} = +58°$ (c=0.65, chloroform).

Empirical formula: $C_{50}H_{62}N_4O_{12}$.

IR (KBr, $cm^{-1}$): 745, 830, 1040–1060, 1210, 1260, 1340, 1380, 1470, 1510, 1620, 1740, 2950, 3500.

EXAMPLE 23

Preparation of N-demethyl-N-(8-hydroxyoctyloxymethyl)-leurosine 2.29 g (13 equivalents) of 1,8-octanediol are added to a solution containing 1.6 g of crude N-demethyl-N-methoxymethylleurosine in 650 ml of dichloromethane. After complete dissolution, the mixture is cooled to +10° C. and the pH value is adjusted to 3 by the portionwise addition of abs. ethereal hydrogen chloride solution. The course of the reaction is followed by TLC (by using a developing system containing dichloromethane and methanol in a ratio of 20:2; the $R_f$ value of the product is lower than that of the starting substance). At the end point of the reaction (after about 20 minutes at +10° C.), the acid is neutralized by adding saturated potassium carbonate solution, and after separating the phases, the aqueous solution is extracted twice with 20 ml of dichloromethane each. The combined organic phase is washed twice with 20 ml of water each, dried over anhydrous magnesium sulphate and evaporated under reduced pressure. The oily residue is dissolved in 10 ml of boiling dichloromethane. After cooling, the precipitate is filtered by suction and washed twice with 5 ml of dichloromethane each to give 1.6 g of 1,8-octanediol. The combined filtrate is evaporated and the residue is purified by column chromatography to give the aimed product in a yield of 370 mg (17%); m.p.: 140°–144° C. (with decomposition); amorphous; $[\alpha]_D = +46°$ (c=1, chloroform); $[\alpha]_{546} = +59°$ (c=1, chloroform).

Empirical formula: $C_{54}H_{72}N_4O_{11}$.

IR (KBr, $cm^{-1}$): 750, 1050, 1230–1260, 1380, 1475, 1510, 1620, 1740, 2950, 3400.

EXAMPLE 24

Preparation of N-demethyl-21'-hydroxy-N-methoxymethylleurosine from N-demethyl-N-methoxymethylleurosine A solution containing 0.15 g of N-demethyl-N-methoxymethylleurosine in 30 ml of dichloromethane is stirred with 0.75 g of activated manganese dioxide at room temperature for 24 hours. Then the solution is filtered through Celite and the Celite layer is washed with 15 ml of dichloromethane. After evaporating the solvent, the residue is purified by column chromatography to give the aimed product in a yield of 76 mg; m.p.: 240° C. (with decomposition); amorphous; $[\alpha]_D = +41°$ (c=1, chloroform); $[\alpha]_{546} = +54°$ (c=1, chloroform).

Empirical formula: $C_{47}H_{58}N_4O_{11}$.

IR (KBr, $cm^{-1}$): 730, 1100, 1200–1240, 1360, 1450, 1490, 1600, 1720, 2850, 3350.

We claim:

1. Bis-indole derivatives of the formula (I)

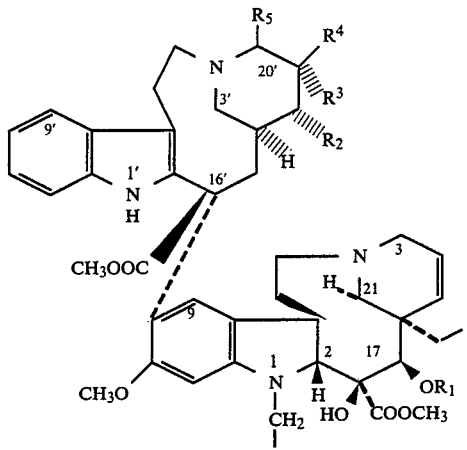

(I)

wherein $R_1$ is a hydrogen atom or an acetyl group;
$R_2$ is a hydrogen atom;
$R_3$ is an ethyl group of α-position;
$R_4$ is a hydroxyl group of β-position; and
$R_5$ is a hydrogen atom;
A is a hydroxyethyl group; and
X is a sulphur atom
and pharmaceutically acceptable acid addition salts thereof.

2. The compound N-demethyl-N-(2-hydroxyethylthiomethyl)vinblastine or pharmaceutically acceptable acid addition salts thereof.

3. The compound 17-deacetyl-N-demethyl-N-(2-hydroxyethylthiomethyl)-vinblastine or pharmaceutically acceptable acid addition salts thereof.

4. A pharmaceutical composition comprising an effective amount of a bis-indole derivative of the formula (I). or a pharmaceutically acceptable acid addition salt thereof as the active ingredient, wherein $R_1$, $R_2$, $R_3$, $R_4$, $R_5$, X and A are as defined in claim 1, and a pharmaceutically acceptable carrier, additive or mixture thereof.

* * * * *